United States Patent
Giuliani et al.

(10) Patent No.: US 8,883,892 B2
(45) Date of Patent: Nov. 11, 2014

(54) ADDUCTS WITH PERFLUOROPOLYETHER PHOSPHATE AND USES THEREOF

(75) Inventors: Giammaria Giuliani, Milan (IT); Anna Benedusi, Milan (IT); Giovanni Pantini, Milan (IT); Antonio Mascolo, Milan (IT); Sergio Baroni, Villa d'Adda (IT)

(73) Assignee: Giuliani S.p.A., Milan (IT)

( * ) Notice: Subject to any disclaimer, the term of this patent is extended or adjusted under 35 U.S.C. 154(b) by 0 days.

(21) Appl. No.: 13/806,754

(22) PCT Filed: Jun. 23, 2011

(86) PCT No.: PCT/IB2011/052756
§ 371 (c)(1),
(2), (4) Date: Dec. 22, 2012

(87) PCT Pub. No.: WO2011/161641
PCT Pub. Date: Dec. 29, 2011

(65) Prior Publication Data
US 2013/0102712 A1   Apr. 25, 2013

(30) Foreign Application Priority Data
Jun. 24, 2010   (IT) .................................. MI10A1149

(51) Int. Cl.
| | |
|---|---|
| C08G 65/00 | (2006.01) |
| A61Q 19/00 | (2006.01) |
| A61K 8/365 | (2006.01) |
| A61K 8/73 | (2006.01) |
| A61K 8/19 | (2006.01) |
| A61K 8/24 | (2006.01) |
| A61Q 17/04 | (2006.01) |
| A61K 8/70 | (2006.01) |
| A61K 8/81 | (2006.01) |
| A61K 8/67 | (2006.01) |
| A61K 8/27 | (2006.01) |

(52) U.S. Cl.
CPC ................ *C08G 65/00* (2013.01); *A61Q 19/00* (2013.01); *A61K 8/365* (2013.01); *A61K 8/732* (2013.01); *A61K 8/19* (2013.01); *A61K 8/24* (2013.01); *A61Q 17/04* (2013.01); *A61K 8/70* (2013.01); *A61K 8/8111* (2013.01); *A61K 8/676* (2013.01); *A61K 8/27* (2013.01)
USPC ............ 524/111; 524/414; 524/430; 524/442

(58) Field of Classification Search
None
See application file for complete search history.

(56) References Cited

U.S. PATENT DOCUMENTS

| | | | |
|---|---|---|---|
| 4,803,067 A * | 2/1989 | Brunetta et al. ................ | 424/63 |
| 2004/0185026 A1 * | 9/2004 | Pantini ....................... | 424/70.23 |
| 2007/0148109 A1 * | 6/2007 | Panin ............................. | 424/62 |

FOREIGN PATENT DOCUMENTS

| | | |
|---|---|---|
| EP | 0890356 A2 | 1/1999 |
| EP | 1074243 A2 | 2/2001 |
| EP | 1762273 A2 | 3/2007 |
| EP | 2420221 | 2/2012 |
| KR | 20040059033 | 7/2004 |
| KR | 20100048594 | 5/2010 |
| WO | WO2010009989 | 1/2010 |

OTHER PUBLICATIONS

Database GNPD [online] Mintel; Jan. 2010.
Pantini et al., Elsevier, Clinics in Dermatology, J.B. Lippincott.
Data Base WPI, Thompson Scientific.
Notification of International Search Report and Written Opinion, PCT/IB2011/052756 mailed Sep. 19, 2012.

* cited by examiner

*Primary Examiner* — Hasan Ahmed
*Assistant Examiner* — Randeep Singh
(74) *Attorney, Agent, or Firm* — DLA Piper LLP (US)

(57) ABSTRACT

The present invention relates, in one aspect, to an adduct of formula O-PF-A, in which O is an oil; PF is a perfluoropolyether phosphate (PFPE phosphate); A is at least one substance selected from: (X) a water-soluble polyhydroxylated substance and (Y) a water-insoluble inorganic substance and to topical applications thereof in particular in the cosmetic and pharmaceutical field.

9 Claims, 2 Drawing Sheets

Scheme for preparation of the O-PF-A adduct by Method a and Method b (*) solid or waxy appearance Preparation of adducts (A = X or Y) by Method a

ADDUCTS WITH PERFLUOROPOLYETHER PHOSPHATE AND USES THEREOF

CROSS REFERENCE TO RELATED APPLICATIONS

This is a U.S. national stage entry of International Application No. PCT/IB2011/052756, filed on Jun. 23, 2011, which in turn claims priority to Italian Patent Application No. MI2010A001149, filed Jun. 24, 2010, each of which is hereby incorporated by reference herein in its entirety.

FIELD OF THE INVENTION

The present invention relates to adducts with perfluoropolyether phosphate and uses thereof.

The present invention relates to the field of products for topical application, in particular to the cosmetic and/or pharmaceutical field.

PRIOR ART

The present invention origins from the need of modifying properties, behaviour and functionality of active substances typically used in the cosmetic and/or pharmaceutical field.

In the chemical-industrial practice, problems of stability of active ingredients and of their performance or activity during use are difficult to solve and often compel industry to identify novel groups of molecules, involving high expenditure on research.

It has been observed that application in the cosmetic or pharmaceutical field even of compounds of undeniable activity is often hampered by difficulties encountered in stabilization of formulations and in performance during application.

As an example, we may mention the problems of stability connected with the use of vitamins and in particular of vitamin C (L-ascorbic acid) as skin lightening agent and in other cosmetic applications.

Vitamin C is in fact unstable in the presence of water, both in the form of sodium ascorbate and as ascorbic acid, and moreover is easily oxidized in contact with oxygen, with degradation that increases as the temperature rises. Owing to this instability, vitamin C is used in the cosmetic industry in the form of derivatives, for example inorganic esters such as phosphates or organic esters such as palmitate, which only offer a partial solution of the problem, because they are not completely stable, or for other reasons. The organic esters of ascorbic acid, for example, are only able to release vitamin C by the action of the enzymes of the skin to a slight extent, so that the desired cosmetic effects are only obtained to a significantly reduced extent.

Conversely, in the case of sunscreens, i.e. products that include UV filters in their formulation to screen solar radiation and allow more prolonged exposure, problems of formulation are encountered.

Currently, in fact, in order to increase the safety profile, there are precise regulatory restrictions regarding the maximum level of an individual UV filter in a sunscreen formulation. For this reason, to obtain an adequate screening effect, sunscreens incorporate more than one UV filter, usually from 3 to 6, to reach a total concentration of 15-20 wt. %, which guarantees a high level of protection, with problems of compatibility and risk of cutaneous absorption.

The increasing demand for sunscreens with a high level of protection therefore means that the cosmetic industry must constantly be looking for new molecules that are able to block the passage of UV radiation of type A and B, that have a favourable toxicologic profile, are easily tolerated once applied on a person's skin and, because of a higher molecular weight, pose no risk of cutaneous absorption.

However, registration of a new substance, classified as "new chemical entity", requires a considerable effort in terms of human and financial capital, especially if the new chemical entity is intended for human applications.

There is therefore a need to be able to take full advantage of applications of substances or active ingredients that are already marketed, by resorting to technologies that increase their applicability.

Thus, dispensers have been developed for cosmetic and pharmaceutical products that are able to combine active ingredients that are unstable or poorly compatible with one another at the moment of use, disposable packaging that allow the active ingredients to come in contact with the air only at the moment of application, preparations of active ingredients in the form of capsules and formulations with stabilized active principles.

Currently, however, it is felt there is a need to overcome the aforementioned problems by increasing the possible applications of active substances that are already on the market.

SUMMARY

One of the general aims of the present invention therefore resides in supplying active ingredients that are already being marketed in a form that increases the possible industrial applications, especially in the cosmetic and pharmaceutical fields.

Another aim of the present invention resides in providing adducts based on perfluoropolyether phosphate in which one of the components is an active substance useful in the cosmetic or pharmaceutical field.

In view of these aims, according to a first aspect of the present invention, adducts are supplied of formula O-PF-A wherein O is an oil,
PF is a perfluoropolyether phosphate (PFPE phosphate),
A is a physiologically acceptable substance, preferably selected from:
  a water-soluble polyhydroxylated substance (X), preferably comprising at least one carboxyl group,
  a water-insoluble inorganic substance (Y), preferably in the form of micronized powder.

Further additional features of the invention are detailed in dependent claims 2-10 appended hereto.

Within the context of the invention, the term adduct (or complex) means structures that are not only a mixture of the components and that are different from chemical entities, having variable proportions of the components.

In particular the adduct of the invention, not having defined proportions of the components and therefore of the various atoms, does not resemble a substance of the daltonide type (resulting from a chemical reaction); moreover, the adduct is not included in the category of non-daltonide or berthollide compounds, which are typically common among inorganic minerals, since it comprises mainly compounds of the organic type that are associated with one another.

Within the context of the invention, the term adduct (or conjugate) does not mean a mixture of the components O, PF, A. The adduct of the invention in fact has an appearance and behaviour that distinguish it from a direct mixture of the components. In fact, it is difficult to obtain a mixture between oil and PFPE owing to the incompatibility between oil (O)

and PF (PFPE phosphate), which is a polymeric material that is highly oil-repellent and is not transportable, unless it is used in aqueous solutions.

Typically, the adduct of the invention can be obtained according to the method described hereunder with proportions of the components that typically vary within limits that form part of the present invention.

In particular, in the O-PF-A adduct of the invention the three components are bound together by weak bonds that maintain its stability. It has been observed that the adduct of the invention is not substantially destructured by prolonged contact with water (e.g. up to two years) or as a result of vigorous mechanical agitation. In water in particular, formation of oil is not observed, and destructuring does not occur even by agitation in the same oil used for its preparation.

Typically, the adduct of the invention is insoluble in water and in oils and is highly oil-repellent.

Typically, the O-PF-A adduct of the invention is amorphous, waxy, semisolid or semifluid.

These characteristics make it suitable for particular applications in the cosmetic and/or pharmaceutical field.

For example, insolubility in water is utilized for incorporating active ingredients that are water-soluble and unstable in water or incompatible with other active ingredients of the aqueous phase. Conversely, oil repellence serves to prevent penetration of the skin, conferring advantages in the case of active ingredients designed for external application on the skin such as UV filters, lightening agents, tanning agents, exfoliating agents, fragrances, ozonized oils. Moreover, on formation of the adduct of the invention, the aforementioned active ingredients behave as if they had a higher molecular weight, leading to a further decrease of penetration of the skin and therefore of the risk of irritation.

DETAILED DESCRIPTION OF THE INVENTION

One of the essential components of the adduct of the invention is an oil (O), i.e. a liquid that is insoluble in water. Oils suitable for the applications of the invention comprise physiologically acceptable oils, in particular those usable in the cosmetic and/or pharmaceutical field.

Typical examples of oils useful within the scope of the invention are emollient oils, UV filters and other oils having a cosmetic and/or pharmaceutical activity and mixtures thereof.

Typical examples of oils endowed with emollient properties comprise:
hydrocarbons, for example mineral oils, paraffins and isoparaffins, low molecular weight polyolefins, squalane, linear and cyclic terpenes,
long-chain alcohols, for example ethylhexyldodecanol, hexyldecanol, isostearyl alcohol, cetearyl alcohol;
ethers of fatty acids, for example caprylic ether;
esters of monocarboxylic fatty acids with synthetic alcohols, for example ethylhexyl palmitate, isopropyl palmitate, isopropyl myristate, isopropyl isostearate, hexyl laurate;
esters of monocarboxylic acids with fatty alcohols, for example $C_{12-15}$ alkyl benzoate, cetyl/stearyl isononanoate;
esters of monocarboxylic fatty acids with fatty alcohols, for example tridecyl stearate, stearyl ricinoleate;
esters of monocarboxylic acids with synthetic alcohols, for example ethylhexyl octanoate;
esters of dicarboxylic acids with synthetic alcohols, for example di-isopropyl adipate, dibutyl adipate, di-isopropyl sebacate, dibutyl sebacate;
esters of dicarboxylic acids with fatty alcohols, for example myristyl adipate;
esters of monocarboxylic acids with propoxylated glycols, for example PEG-4 diheptanoate;
esters of fatty acids with poly-hydroxylates, for example esters of ascorbic acid such as ascorbyl stearate, ascorbyl palmitate, or glycerol tricaprylate/caprate, pentaerythritol tetracaprylate/caprate, pentaerythritol tetraoleate, alkyl esters of sucrose;
esters of hydroxy acids with fatty alcohols, for example tridecyl salicylate, myristyl tartrate, myristyl lactate, tri-$C_{12-13}$alkyl citrate;
esters of polycarboxylic acids with fatty alcohols, for example tridecyl trimellitate;
vegetable oils, for example avocado oil, macadamia oil, castor oil, sesame oil, almond oil, wheat germ oil, jojoba oil, sunflower seed oil;
hydrogenated vegetable oils;
non-saponifiable fractions of vegetable oils;
animal oils, for example lanolin oil.

Typical examples of oils that possess an activity of the cosmetic or pharmaceutical type and/or functional oils comprise:
UV filters (for sunscreens) of the chemical type in liquid form, for example ethylhexyl methoxycinnamate (Parsol MCX from DSM, the Netherlands) or octocrylene (Uvinul A539 from BASF, Germany) or also in solid form, if soluble in liquid filters or in emollient oils such as butylmethoxydibenzoylmethane (Parsol 1789 from DSM);
essential oils or fragrances (synthetic and natural, combinations thereof) as such or in solution in emollients;
polyunsaturated acids, for example omega-3, omega-6, omega-9;
ozonized vegetable oils, for example sunflower oil through high content of an unsaturated acid such as ricinoleic acid;
fat-soluble vitamins, for example fatty esters of vitamin C; vitamin E and its derivatives such as vitamin E acetate with antioxidant (anti-ageing) properties;
silicone oils for example dimethicones and alkyl dimethicones;
perfluoropolyethers, for example perfluoropolyethers of type Y and Z, dialcoholic perfluoropolyethers and ethoxylated dialcoholic perfluoropolyethers.

In certain embodiments the oil is present in the adduct of the invention in an amount greater than or equal to 10 wt. % relative to the PFPE phosphate, in particular in the case of an oil with MP=250.

Another essential component of the adduct of the invention is perfluoropolyether phosphate (PF or PFPE phosphate) obtained by reaction of esterification of orthophosphoric acid or phosphoric anhydride or phosphorus oxytrichloride with an ethoxylated α,ω-perfluoropolyether dialcohol, a compound with the structure of a linear polymer with two hydroxyls in the end positions, having the following formula:

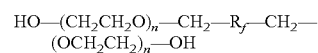

in which: n=1-2

Accordingly, the reaction of esterification (between dialcohol and acid) leads to a bifunctional derivative. Typically, orthophosphoric acid also comprises more than one reactive position (in particular three), with the possibility of having mono-, di- and triesterification. Typically the mixture of esters is called "phosphate", even if the monoester predominates over the diester and the triester component is very reduced or absent because the reaction is carried out with excess of orthophosphoric acid, in particular to avoid formation of the triester, which is insoluble in water.

The perfluoropolyether phosphate (PFPE phosphate) used within the scope of the invention has the following simplified formula (monoester):

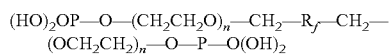

in which:

represents a (per)fluoropolyether chain:
  with random distribution of —CF$_2$CF$_2$O— and —CF$_2$O— units,
  with p/q=0.5-3.0,
  n=1-2.

In certain embodiments, with MW of about 1500, p is between 6 and 12 and q is between 10.8 and 3.6. On modifying the polymerization conditions, different values are obtained, with minimal differences for performance.

In some embodiments the average molecular weight of Rf is from 500 to 4000, typically from 1000 to 2000, preferably from 1400 to 1600. In certain embodiments, MW is approx. 1500, for example as in the case of the product marketed with the brand name Fomblin HC/P2-1000. Chemically this polymer is a phosphoric acid ester and typically is in the form of a viscous liquid that is insoluble in water, but can be solubilized by neutralization.

A description of a suitable PFPE polymer is given in international patent application WO 2010/009989 A1 in the name of the same applicant, the contents of which are incorporated here by reference.

Typically, the PFPE phosphate of one embodiment corresponds to a precise INCI name: "Polyperfluoroethoxymethoxy Difluoroethyl PEG Phosphate".

According to one embodiment the chain of PFPE (R$_f$) is linear and symmetric (perfluoropolyether of type Z), with —CF$_2$CF$_2$O— and —CF$_2$O— units distributed randomly, and is obtained by photopolymerization of tetrafluoroethylene in the presence of oxygen.

Structurally it is the chain of a copolymer, even if we start from a single monomer, which is partially degraded by a radical mechanism that involves oxygen and is activated by UV radiation.

Typically, a chain of PFPE with molecular weight of 1500 corresponds to an average molecular weight (MW) of PFPE phosphate of 2500. This MW arises from the contributions to the average value of the phosphate groups, of the oxyethylene group and of the diester in which there are two PFPE chains bound to one and the same phosphate group.

According to certain embodiments, aqueous solutions of PFPE phosphate can be prepared in two ways: solubilization in water by neutralization and solubilization in a polar solvent and subsequent dilution with water, for example as described below.

Solubilization in Water by Neutralization

According to a first embodiment the PFPE phosphate can be dissolved in water by partial or total neutralization with a base. Typically sodium hydroxide dissolved in water is used, but other alkalies or an organic base can be used. The neutralizing agent is added gradually to the aqueous dispersion of PFPE phosphate, preferably working hot (60-90° C.) and with stirring: clear solutions are obtained with pH typically between 4 and 12, preferably between 5 and 7, and concentrations of PFPE phosphate in the range 5-20%, optionally to be diluted to the concentrations suitable for addition of water.

Solubilization in Water Via Polar Solvent

According to another embodiment, aqueous solutions of PFPE phosphate are obtained without the use of neutralizing agents by preparing concentrated solutions, for example up to 40-50 wt. %, in polar solvents, to be diluted by gradual addition of water which is to be the main component of these solutions, with concentrations of PFPE phosphate advantageously in the range 5-20%, for which further dilutions with water are possible, to reach suitable concentrations which are even very low, for example less than or equal to 0.1 wt. %.

The pH of these solutions can vary advantageously from 1.5-2 up to neutrality by the possible addition of a neutralizing agent. A suitable solvent can be a volatile solvent, for example ethanol, propanol, isopropanol, acetone, methylal; or a glycol, for example ethylene glycol, propylene glycol, 1,4-butanediol, 1,2-pentanediol, 1,6-hexanediol, dipropylene glycol; or a glycol-ether, for example diethylene glycol monoethyl ether, dipropylene glycol monoethyl ether and mixtures thereof. Preferred solvents comprise ethanol, isopropanol, propylene glycol, 1,2-pentanediol and mixtures thereof. In these conditions, typically in an aqueous-alcoholic or aqueous-glycolic environment with a preponderance of water, any type of oil is insoluble.

Another component of the adducts of the invention comprises at least one substance or compound A selected from the two classes:

(X) polyhydroxylated substances, typically water-soluble, preferably comprising at least one carboxyl group;
(Y) inorganic substances insoluble in water, preferably in the form of micronized powder.

Within the scope of the invention, suitable soluble polyhydroxylated compounds or substances (X) are those that find application in the cosmetic and/or pharmaceutical field. According to one embodiment the soluble poly-hydroxylated substances are selected from the group comprising:

ascorbic acid and related salts (for example sodium ascorbate), arbutin and kojic acid, for example to be used as skin lightening agents,
  other polyhydroxylated substances, for example lactic acid, citric acid, tartaric acid and related salts, for example to be used as exfoliating agents or erythrulose to be used as tanning agent.

In some embodiments, said polyhydroxylated substances (X) are soluble hydroxylated organic acids, in particular polyhydroxylated carboxylic acids. Typical examples of suitable carboxylic acids comprise lactic, tartaric, citric, glycolic acids and mixtures thereof.

Suitable water-insoluble inorganic substances or compounds (Y) are those that find application in the cosmetic and/or pharmaceutical field. Preferably the water-insoluble inorganic substances are in the form of micronized powder, for example having particle size between 1 and 50 micron, preferably between 3 and 10 micron.

According to one embodiment, the water-insoluble inorganic substance can be produced synthetically or can be of mineral origin, and in particular is selected from the group comprising:

metal oxide, for example zinc oxide, iron oxides, titanium dioxide (solar), chromium oxides, bismuth oxychloride, sulpho-silicates and mixtures thereof
  phosphate minerals, for example hydroxyapatite;
  silicate minerals, for example talc, mica, bentonite and mixtures thereof.

In one embodiment, functional combinations of oil (O) and of the substances or compounds X, Y described above are envisaged, for the purpose of obtaining synergistic effects. Typical examples comprise the following combinations:

lightening and exfoliating agents, for example for making cosmetic products for the face with anti-ageing effect;

UV filters in combined form of oils (chemical filters) and insoluble powders (physical filters) for obtaining sunscreens with high level of protection, water-soluble vitamins, for example vitamin C, with fat-soluble vitamins, for example fatty esters of the same vitamin C or vitamin E, for increasing antioxidant activity (combined anti-free radical and anti-ageing action).

According to another aspect of the invention, methods are provided for preparing the O-PF-A adducts described above.

According to one embodiment, a method (method A) is provided for preparing an O-PF-A adduct comprising a stage of addition of an aqueous solution of PF (PFPE phosphate) typically with stirring, to make an O-PF emulsion, a stage of addition of an aqueous solution or dispersion of substance A to the O-PF emulsion, typically with stirring, to form the O-PF-A adduct, which is generally precipitated or separated in some way.

In some embodiments, the precipitate obtained, based on the O-PF-A adduct, is separated by filtration or decanting, optionally after centrifugation.

According to another embodiment, a method (method B) is provided for preparing an O-PF-A adduct comprising a stage of addition of a solution of PF to an aqueous solution or dispersion of substance A, typically with stirring, to form the adduct PF-A and a stage of addition of an oil (O) to the adduct PF-A, typically with stirring, to form the O-PF-A adduct.

In certain embodiments, the stages of dispersion of the water-insoluble components in both methods described above are carried out with vigorous stirring, for example of the mechanical type typically obtained by using a turbine.

It has been observed that the method of preparation described leads to a homogeneous adduct being obtained, substantially free from separated oil.

According to another aspect of the present invention, an O-PF-A adduct is supplied in which O, PF, A are as previously defined, obtained with method A or method B described above.

Specifically, with the first of the methods (method A) described above, the following O-PF-A adducts are obtained at yields of approx. 90%:

| O | PF | A (X, Y) |
|---|---|---|
| Cosmetic emollient oil | PFPE phosphate | Sodium ascorbate (X) |
| UV sun filter oil | PFPE phosphate | Sodium ascorbate (X) |
| UV sun filter oil | PFPE phosphate | Ascorbic acid |
| Cosmetic emollient oil | PFPE phosphate | Zinc oxide (Y) |
| UV sun filter oil | PFPE phosphate | Hydroxyapatite (Y) |
| UV sun filter oil | PFPE phosphate | Talc (Y) |

BRIEF DESCRIPTION OF THE DRAWINGS

Further characteristics of the O-PF-A adducts according to the present invention and of technologies for preparing them will become clearer from the appended figures in which:

FIG. 1 is a schematic representation of two alternative routes for preparing the adduct according to the invention.

Figure 1:
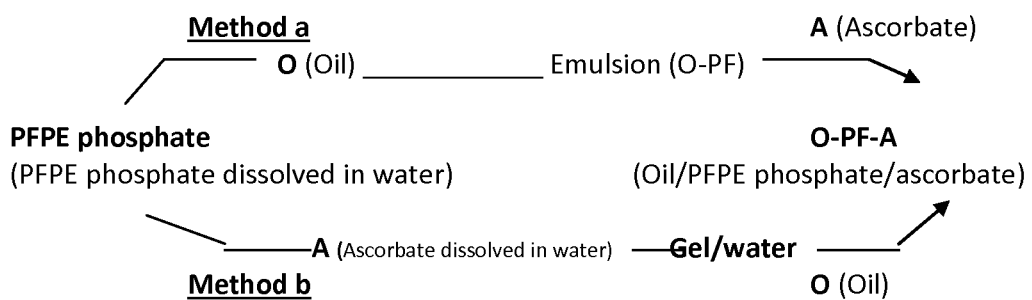
FIG. 1 shows schematically two methods (Method A and Method B) for making the O-PF-A adduct (as an example A=ascorbate)
Figure 2:
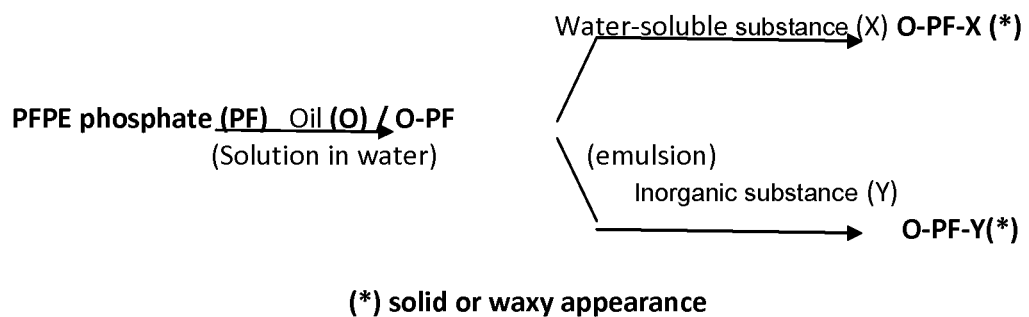
FIG. 2 shows schematically the preparation of two types of complexes (A=X or Y) using Method A.

The method that envisages preparing an oil-perfluoropolyether phosphate (O-PF) dispersion as intermediate is shown schematically in greater detail in FIG. 2, in which component A of the adduct can be selected from the substances or compounds X, Y described above.

According to some embodiments, the ratio of the amount of component PF relative to the amount of the oil component (O) added to that of component A is in the following range:

|  | 0.01 | < | PF/O +A (X,Y) | < | 50, |
|---|---|---|---|---|---|
| preferably: | 0.1 | < | PF/O + A (X,Y) | < | 5, |
| and more preferably: | 0.2 | < | PF/O + A (X,Y) | < | 1 | where: PF=PFPE phosphate, O=oil, A is a substance selected from X, Y in which X=polyhydroxylated substance, Y=inorganic substance, as described above.

It has moreover been observed that, at equal content of PFPE phosphate and equal ratio of PFPE phosphate to the sum of the other two components (O, A), the ratio between these last two (O, A) can also vary in a range from 0 to 100%, i.e. it is possible to have adducts with two components: with oil only, or with only soluble hydroxylated substance or micronized powder. When selecting this ratio it should be borne in mind that the oil (O) or component A (X and/or Y), or both, can perform functionalities as an active principle that can be increased by increasing its concentration, at the expense of the component that has less important functionalities (activities).

Typically two components O and A can have the same order of magnitude, and in other embodiments O has a concentration 5-10 times greater than that of A and vice versa (but in fact it is not practical to go beyond these limits for the relative proportions of the components).

According to another aspect, the present invention relates to a cosmetic or pharmaceutical composition comprising at least one physiologically acceptable excipient and an adduct according to any one of claims 1-9.

The composition according to the this aspect of the invention can comprise one or more cosmetically or pharmaceutically acceptable excipients commonly used in cosmetic or pharmaceutical formulations.

In some embodiments the adduct is present in an amount between 0.01 and 10 wt. % relative to the total weight of the composition, preferably from 0.1 to 5 wt. %.

The following examples are provided purely for illustrating the present invention and are not to be regarded as limiting the scope of protection as results from the appended claims.

EXAMPLES

Specifically, example 1 describes a method that comprises the addition, with simple manual stirring, of a dilute (2%) aqueous solution of a perfluoropolyether phosphate (PFPE phosphate) to a concentrated solution (16%) of sodium ascorbate. Initially there is clouding and then flocculation with formation of an adduct in the form of a gelatinous sediment. This sediment was not found to be stable in the air after separation by decanting the aqueous phase.

A similar adduct is obtained when the two components are mixed in a different order, i.e. by adding the solution of sodium ascorbate to that of PFPE phosphate (example 2), or by working with different ratios of PFPE phosphate to sodium ascorbate (example 3). The adduct of the invention does not form when sodium ascorbate is replaced with ascorbic acid (examples 4 and 5).

However, it is observed that, by working in the presence of a small amount of an oil of medium polarity such as for example ethylhexyl palmitate and applying stirring, preferably for example using a turbine, it is possible to obtain, by precipitation, an adduct of a whitish appearance, in larger amount and with an evident greater stability (example 6).
Typically, the yield in preparation of the adduct decreases on increasing the concentration of ethylhexyl palmitate with the other ingredients remaining the same (example 7), while it increases with the content of said oil and of PFPE phosphate (examples 8 and 9) when their ratio is kept constant (as a guide, around 0.5% as in example 6). On replacing the oil of medium polarity such as ethylhexyl palmitate with an apolar oil such as mineral oil, there were no significant differences (example 10).
Employing the embodiment of method a) described above, other tests were carried out (examples 11-13) in which ethylhexyl palmitate is replaced with variable amounts of a sun filter (ethylhexyl methoxycinnamate), emulsified with a constant quantity of PFPE phosphate. The emulsions thus obtained are combined with sodium ascorbate in variable proportions, as shown in Table I. The results of these tests confirm that the characteristics of the oil used are not decisive for the purpose of attainment of the result and that it is possible to replace emollient oils with active oils such as UV sun filters.
In another series of tests (examples 14-16) sodium ascorbate was replaced with ascorbic acid, still obtaining formation of adducts that do not form in the absence of oil (comparison between examples 14-16 and examples 4-5). It should be pointed out that the procedure was modified relative to the preceding series, demonstrating the importance of carrying out, as a first step, dispersion of the oil in water, whereas it makes no difference whether ascorbic acid is added with or without combination with PFPE phosphate (in confirmation, in the case of examples 14-16 separation of oil is not observed).
The following equipment and instruments were used for carrying out the procedures described in the examples:
- Turbine: Silverson L5M homogenizer, from Silverson Machines Ltd., Waterside, Chesham (United Kingdom), with standard head and standard molecular-sieve stator and in-line head;
- Magnetic stirrers with heating plate;
- Heraeus Multifuge X1R centrifuge, with thermal regulation, Thermo Electron LED GmBH, D-37520 Osterode (Germany);
- Metrohm pH-meter, with combined glass electrode and probe for temperature control, Metrohm A G, Herisau (Switzerland);
- Brookfield DV-I viscosimeter, spindle set, Brookfield Engineering Laboratories Inc., Middleboro, Mass. (USA);
- FT-IR spectrophotometer, AVATAR 330, with HATR technology and Smart Performer accessory, Thermo Fisher Scientific, Waltham, Mass. (USA);
- Thermometers.

For purposes of illustration, the examples have been divided into groups having component A of the O-PF-A adduct as the main variable, since PFPE phosphate is a component that is always present and typically every type of oil can be used with the other two components. The examples were then divided into 3 main groups:
- Group 1: examples 1-16 with sodium ascorbate and ascorbic acid,
- Group 2: examples 17-20 with other polyhydroxylated substances,
- Group 3: examples 21-23 with water-insoluble inorganic substances, Specifically, some preparations are described (Examples 1-5, 17, 19) which are not included among the adducts of the invention and others (Examples 6-16, 18, 20-23) which, conversely, qualify as adducts (or complexes) according to the invention.

Group 1: Examples with Sodium Ascorbate and Ascorbic Acid

Example 1

Example 1

Preparation of an Adduct with Two Components: PFPE Phosphate and Sodium Ascorbate (the Adduct without the Oil Component is More Water-Soluble and in Every Case has Low Stability in the Air)

Solubilization of PFPE phosphate, commercially available as water-insoluble phosphoric acid ester (commercial product Fomblin HC/P2-1000, made by Solvay Solexis SpA, Milan), is carried out separately. Solubilization is effected by neutralization of the aqueous dispersion of Fomblin HC/P2-1000 heated to 80° C. Neutralization requires great care, with gradual addition of a solution of sodium, hydroxide (18%) and monitoring of pH, in order to prevent shock, and maintaining magnetic stirring, as follows:

Aqueous Solution
  Sodium hydroxide 0.76 parts
  Demineralized water 8.00 parts
Aqueous Dispersion
  PFPE phosphate (Fomblin HC/P2 1000) 20.00 parts
  Demineralized water 71.24 parts
Total 100.00 parts (containing 20 parts by weight of PFPE phosphate)

A solution of PFPE phosphate (20%) is obtained that is perfectly clear, of a pale yellow colour, with pH between 5.5 and 7.5, which can be diluted with water to the appropriate concentration.

In this example, as in the subsequent examples, preparation is carried out by working with a total of 200 g of reactants, including water, stating the percentages by weight of the reactants.

A solution of PFPE phosphate (pH=7.2) is added to a solution of sodium ascorbate (DSM, the Netherlands) with light manual stirring, working with the following proportions (PFPE phosphate/sodium ascorbate ratio by weight: 2:16 with reference to PFPE phosphate 100%):

|   |   | % |   |
|---|---|---|---|
| a) | PFPE phosphate (20 wt. %) | 10 | (2% of 100% PFPE phosphate) |
| b) | Sodium ascorbate | 16 |   |
|   | Water | 74 |   |
|   | Total | 100 |   |

Following addition, the solution first becomes turbid, then after standing for about ten minutes, flocculation occurs, with formation of a sediment (adduct) which is in the form of a translucent gel, with a volume of approx. 20% of the total, whereas the aqueous phase is clear and slightly yellow. After two weeks on the shelf, the gel under the aqueous layer does not seem to have changed, whereas the overlying aqueous solution has a reddish-brown coloration. After separation by decanting, the gel (soluble in water, almost insoluble in alcohol and difficulty dispersible in oils) proves to be unstable in the air.

Example 2

Comparison (with Different Procedure)

Example 1 was repeated, working with the same proportions but with a different procedure: the aqueous solution of sodium ascorbate is added to that of PFPE phosphate, with entirely similar results (in particular the adduct is not stable).

Example 3

PFPE Phosphate with Sodium Ascorbate (with Lower Ratio)

Example 1 was repeated adopting the same procedure but working with a lower ratio of PFPE phosphate to sodium ascorbate:

|    |                           | %   |
|----|---------------------------|-----|
| a) | PFPE phosphate (20% in water) | 5   |
| b) | Sodium ascorbate          | 15  |
|    | Water                     | 80  |
|    | Total                     | 100 |

The result was entirely similar to example 1, but flocculation (and adduct formation) was more immediate and with a visibly higher yield.

Example 4

PFPE Phosphate and Ascorbic Acid

Example 1 was repeated adopting the same procedure and the same proportions, but replacing sodium ascorbate with ascorbic acid (DSM, the Netherlands):

|    |                           | %   |
|----|---------------------------|-----|
| a) | PFPE phosphate (20% in water) | 10  |
| b) | Ascorbic acid             | 16  |
|    | Water                     | 74  |
|    | Total                     | 100 |

After two days on the shelf, the solution is no longer perfectly clear, but sedimentation is not observed and therefore there is no adduct formation.

Example 5

Acid PFPE Phosphate and Ascorbic Acid (Comparison)

The same proportions are used as in example 4, but the PFPE phosphate presolubilized in water is replaced with acid PFPE phosphate (i.e. without neutralization of the commercial product) dissolved directly in ethanol and then diluted with water.

|    |                           | %   |
|----|---------------------------|-----|
| a) | Acid PFPE phosphate (100%) | 2   |
|    | Ethanol (95%)             | 20  |
|    | Water                     | 16  |
| b) | Ascorbic acid             | 16  |
|    | Water                     | 46  |
|    | Total                     | 100 |

The result is entirely similar to that of example 4, i.e. there is no sedimentation and therefore no adduct formation.

Example 6

PFPE Phosphate, Ethylhexyl Palmitate and Sodium Ascorbate

The following operations are carried out: preparation of a dilute emulsion (a) of ethylhexyl palmitate (Cegesoft C24, Cognis, Germany) in water by adding the oil to an aqueous solution of PFPE phosphate (20%) stirring with a turbine for about 5 minutes; addition of this dispersion to an aqueous solution of sodium ascorbate (b), with manual stirring followed by turbine stirring:

|    |                               | %     |
|----|-------------------------------|-------|
| a) | Ethylhexyl palmitate          | 0.5   |
|    | Water                         | 29.5  |
|    | PFPE phosphate (20% in water) | 5.0   |
| b) | Sodium ascorbate              | 15.0  |
|    | Water                         | 50.0  |
|    | Total                         | 100.0 |

Following addition of the emulsion to the solution of sodium ascorbate, clouding is observed immediately, followed by flocculation with formation of a whitish sediment.

At the end of flocculation, and after standing for some minutes, the aqueous part above the sediment is clear. On stirring, there is no redistribution of the sediment (adduct). The volume of this sediment, with the appearance of a solid, is approx. 20-25% of the total. After standing on the shelf for about a fortnight, the aqueous phase has a red coloration. The deposit, separated by decanting, is insoluble in oils and in water, is oil-repellent and apparently stable in the air.

Example 7

PFPE Phosphate, Ethylhexyl Palmitate and Sodium Ascorbate (Comparison with Example 6)

Example 6 is repeated, increasing the oil content (2% instead of 0.5%), keeping the content of the other ingredients constant and adopting the same procedure: the result is similar with respect to the characteristics of the adduct (sediment), but it forms in a visibly smaller amount.

Example 8

PFPE Phosphate, Ethylhexyl Palmitate and Sodium Ascorbate (Comparison with Example 6)

Example 6 is repeated with the same procedure, working with larger amounts both of ethylhexyl palmitate and of PFPE phosphate, but with the same ratio (0.5), and with a smaller content of ascorbate:

|   |   | % |   |
|---|---|---|---|
| a) | Ethylhexyl palmitate | 2.5 |   |
|   | Water | 22.5 |   |
|   | PFPE phosphate (20% in water) | 25.0 | (5% of 100% PFPE phosphate) |
| b) | Sodium ascorbate | 7.5 |   |
|   | Water | 42.5 |   |
|   | Total | 100.0 |   |

The result is similar with respect to the characteristics of the adduct (sediment), but it forms in a visibly larger amount. Moreover, after standing for a period of time, no change is observed in the colour of the aqueous phase, which is just slightly coloured yellow.

Example 9

PFPE Phosphate, Ethylhexyl Palmitate and Sodium Ascorbate (Comparison with Example 8)

Example 8 is repeated, working with the same ingredients and proportions, but with a different procedure: a solution of PFPE phosphate (a) is added gradually, with manual stirring, to an aqueous solution of sodium ascorbate (b), then ethylhexyl palmitate (c) with turbine stirring:

|   |   | (%) |
|---|---|---|
| a) | PFPE phosphate (20% in water) | 25.0 |
| b) | Sodium ascorbate | 7.5 |
|   | Water | 65.0 |
| c) | Ethylhexyl palmitate | 2.5 |
|   | Total | 100.0 |

The overall result is visibly different, in particular because unemulsified oil is observed on the surface and there is less formation of adduct (sediment), which looks entirely similar to the adduct of the preceding example.

Example 10

PFPE Phosphate, Mineral Oil and Sodium Ascorbate

Example 8 is repeated except that ethylhexyl palmitate is replaced with mineral oil (BFR070 Paraffinum Liquidum, ACEF SpA, Piacenza):

|   |   | (%) |
|---|---|---|
| a) | Mineral oil | 2.5 |
|   | Water | 22.5 |
|   | PFPE phosphate (20% in water) | 25.0 |
| b) | Sodium ascorbate | 7.5 |
|   | Water | 42.5 |
|   | Total | 100.0 |

The amount of adduct (sediment) and its characteristics are similar to those of example 8, in particular presence of oil is not observed.

Examples 11-13

PFPE Phosphate, Ethylhexyl Methoxycinnamate and Sodium Ascorbate

Example 8 was repeated, replacing ethylhexyl palmitate with the sun filter ethylhexyl methoxycinnamate (Parsol MCX, DSM, the Netherlands), working with the same procedure but variable proportions of the ingredients. The following are prepared:
- emulsions of methoxycinnamate with the same content (5%) of 100% PFPE phosphate and variable content of oil;
- a 30% solution of sodium ascorbate in water.

With manual stirring followed by a brief treatment with a turbine, variable amounts of the solution of sodium ascorbate are added to the dispersion, but so as to have the same total amount of methoxycinnamate combined with ascorbate (15%) and of the three ingredients (20%) as given in Table I.

TABLE I

PFPE phosphate in equal ratio to the sum of ethylhexyl methoxycinnamate and sodium ascorbate.

|   |   | Example 11 | Example 12 | Example 13 |
|---|---|---|---|---|
|   | Ratio: PFPE phosphate (100%)/Methoxycinnamate + ascorbate | 0.33 (%) | 0.33 (%) | 0.33 (%) |
| a) | Ethylhexyl methoxycinnamate | 3.75 | 7.50 | 11.25 |
|   | Water | 33.75 | 42.50 | 51.25 |
|   | PFPE phosphate | 25.00 | 25.00 | 25.00 |
|   | (20% in water) |   |   |   |
|   | Sub-total | 62.5 | 75.0 | 87.5 |
| b) | Sodium ascorbate | 11.25 | 7.50 | 3.75 |
|   | Water | 26.25 | 17.50 | 8.75 |
|   | Sub-total | 37.5 | 25.0 | 12.5 |
|   | Total | 100.00 | 100.00 | 100.00 |

It can be seen that there is a larger amount of deposit in the case of examples 11 and 12, which are treated differently.

Example 11

After three months of ageing on the shelf, no colour change of the adduct or sediment is observed (whitish), and only the aqueous phase assumes a slight reddish coloration. 191.2 g (corresponding to initial 200 g) were centrifuged, in order to separate, by decanting, 141.4 g as aqueous phase and 49.8 g as wet sediment. This adduct was dried in a stove at 45° C. for three days: the dry adduct is apparently unchanged, has a weight of 38.2 g, with a yield of 95.5% relative to a theoretical weight of 40 g (assuming recovery of all three ingredients in insoluble form).

The following treatments are carried out:
- by treating about 9 g with 30 g of ethanol, a yellow solution is obtained, and a whitish deposit; on repeating the treatment with ethanol, a colourless solution is obtained, while the deposit appears entirely similar to the adduct;
- by treatment with water, a slightly yellow solution is obtained, with a deposit similar to that obtained by treatment with ethanol;
- also treatment of 30 g of ethylhexyl methoxycinnamate (Parsol MCX) does not seem to affect the characteristics of the deposit.
- by treatment with 30 g of an O/W emulsion with increased internal phase (75%), containing 1% of PFPE phosphate and 75% of mineral oil, there is good dispersion of the adduct.

Example 12

After ageing for 23 months on the shelf, the adduct of example 12 appears to be unchanged (whitish), and the solution has maintained the same initial yellow coloration. 189.2 g (corresponding to initial 200 g) are centrifuged at 7000 rpm for 10 minutes, in order to separate, by decanting, 148.7 g as aqueous phase and 40.5 g as wet adduct. This adduct was dried in a stove at 40° C. for three days, with no change in appearance and with weight change to 38.7 g, with a yield of 96.7% relative to a theoretical weight of 40 g (assuming recovery of all three ingredients in insoluble form).

Example 14-16

PFPE Phosphate, Ethylhexyl Methoxycinnamate and Ascorbic Acid

One emulsion and two solutions are prepared:
 a) emulsion containing 15% of ethylhexyl methoxycinnamate and 10% of PFPE phosphate,
 b) solution containing 26.5% of ascorbic acid,
 c) 20% solution of PFPE phosphate in water (pH=7.2).

The three components are combined in the proportions shown in Table II.

The procedure adopted envisages, as a first step, emulsification of the oil, combining the ascorbate with PFPE phosphate: solution c) is added to solution b) and is left to stand: no flocculation occurs; dispersion a) is added to the sum of the two solutions: only in the case of example 14, there is clouding almost immediately followed by flocculation and formation of sediment; however, after standing for a few days, in all three examples there is sediment, in almost equal amount.

Table II

PFPE phosphate in various proportions with the sum of ethylhexyl methoxycinnamate and ascorbic acid.

| Ratio: PFPE phosphate (100%)/ Methoxycinnamate + ascorbic acid | | Example 14 0.6% | Example 15 0.5% | Example 16 0.4% |
|---|---|---|---|---|
| a) | Ethylhexyl methoxycinnamate | 3.75 | 7.50 | 11.25 |
| | PFPE phospate (20% in water) | 6.25 | 12.50 | 17.75 |
| | Water | 15.00 | 30.00 | 46.00 |
| b) | Ascorbic acid | 9.75 | 6.50 | 3.25 |
| | Water | 27.75 | 18.50 | 9.25 |
| c) | PFPE phosphate (20% in water) | 7.50 | 5.00 | 2.50 |
| | Water | 30.00 | 20.00 | 10.00 |
| | Total | 100.00 | 100.00 | 100.00 |
| | pH | 2.9 | 3.0 | 3.3 |

After a period of ageing on the shelf (9 months) the sediment (adduct) has a slight red coloration, more evident in the case of examples 14 and 15, but no other changes are observed after a total ageing time of 23 months.

Example 15 193.2 g (corresponding to initial 200 g) were centrifuged at 7000 rpm for 10 minutes, obtaining a solid deposit that can be separated easily from the mother liquor by decanting: this results in 159.8 g as aqueous phase and 33.4 g as wet sediment. This adduct was dried in a stove at 40° C. for two days: the dry adduct is apparently unchanged, has a weight of 31.9 g, with a yield of 74.2% relative to a theoretical weight of 43.00 g (assuming recovery of all three ingredients in insoluble form).

Group 2: Examples with Other Water-Soluble Poly-Hydroxylated Substances

Example 17

PFPE Phosphate and Sodium Lactate

Example 1 is repeated, replacing the solution of sodium ascorbate with a 20% solution of sodium lactate (ACEF, Piacenza), working with the following proportions (2:16):

| | Solution: | % |
|---|---|---|
| a) | PFPE phosphate (20 wt. %) | 10 |
| b) | Sodium lactate (20 wt. %) | 90 |
| | Total | 100 |

The solution of PFPE phosphate is added to the solution of sodium lactate: clouding is observed, followed by flocculation and formation of sediment of a gelatinous appearance (adduct).

Example 18

PFPE Phosphate, Ethylhexyl Palmitate and Sodium Lactate

Example 17 is repeated, replacing the solution of PFPE phosphate with an emulsion containing 1% of ethylhexyl palmitate and 2% of PFPE phosphate (100%):

| | | % |
|---|---|---|
| | Dispersion: | |
| a) | Ethylhexyl palmitate | 1.0 |
| | PFPE phosphate (20%) | 10.0 |
| | Water | 9.0 |
| | Solution: | |
| b) | Sodium lactate (20 wt. %) | 80.0 |
| | Total | 100.0 |

On adding the emulsion to the solution of sodium lactate, at first there is clouding, followed by flocculation and formation of a whitish sediment (adduct) under an almost clear aqueous phase. The sediment does not disperse with stirring.

Examples 19

PFPE Phosphate and Sodium Citrate

Example 17 is repeated, replacing the solution of sodium lactate with a 20% solution of sodium citrate (ACEF, Italy) with a similar result.

Example 20

PFPE Phosphate, Ethylhexyl Palmitate and Sodium Citrate

Example 18 is repeated, replacing the solution of sodium lactate with a 20% solution of sodium citrate, with a similar result.
Group 3—Examples with Water-Insoluble Inorganic Substances

Example 21

PFPE Phosphate, Ethylhexyl Methoxycinnamate and Zinc Oxide

A dispersion of zinc oxide (LSM, Italy) in water is prepared, which is in the form of a milk. This dispersion is added with manual stirring, followed by turbine stirring, to a dispersion containing ethylhexyl methoxycinnamate and PFPE phosphate, working with the following proportions:

|   |                           | %     |
|---|---------------------------|-------|
| a)| Ethylhexyl methoxycinnamate | 2.5   |
|   | PFPE phosphate (20%)       | 25.0  |
|   | Water                     | 22.5  |
| b)| Zinc oxide                | 7.5   |
|   | Water                     | 42.5  |
|   | Total                     | 100.0 |

There are no immediate changes, but then an increase in viscosity of the preparation is observed, and a tendency to form a sediment. After standing (for a few days) centrifugation is carried out, working with 188.6 g: after centrifugation, the aqueous phase (147.4 g) is separated by decanting, obtaining a wet sediment of 41.2 g. It is dried in a stove at 45° C. for two days, obtaining a dry residue of 24.9 g at a yield of around 83% relative to the theoretical amount (30 g) assuming that all three ingredients make up the complex.
Observation by FT-IR shows that the sample is to be regarded as homogeneous. About 1.5 g is treated with ethanol in two steps (20 ml+20 ml), with a residue (non-solubilized powder) of 60% relative to a theoretical 50%: when analysed with FT-IR, this residue shows the presence of unextracted PFPE phosphate (10-25% of the powder).

Example 22

PFPE Phosphate, Methoxycinnamate and Hydroxyapatite (Phosphate Mineral)

Example 21 is repeated, replacing zinc oxide with hydroxyapatite (Apalight, Kalichem Italia) with the same procedure and the same proportions. There is similar behaviour with respect to formation of sediment (adduct). After treatment in the stove at 45° C., an apparently dry residue of 37.2 g is obtained, compared with a theoretical 30 g: FT-IR shows that this sample is also homogeneous, while extraction (20 ml+20 ml of ethanol) leads to an insoluble residue of 52% (relative to a theoretical 50%).

Example 23

PFPE Phosphate, Methoxycinnamate and talc (Silicate Mineral)

Example 21 is repeated, replacing zinc oxide with talc, adopting the same procedure and the same proportions and with similar behaviour with respect to formation of sediment (adduct), which FT-IR shows to be homogeneous.

The invention claimed is:

1. Adduct consisting essentially of

O-PF-A wherein
O is an oil,
PF is a perfluoropolyether phosphate (PFPE) having the formula:

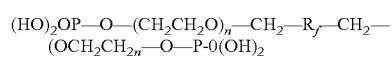

and wherein
$R_f$=—$(CF_2CF_2O)p$-$(CF_2O)_q$ represents a (per)fluoropolyether chain:
with random distribution of —$CF_2CF_2O$— and —$CF_2O$— units,
with p/q=0.5-3.0
n=1-2
and the average molecular weight of $R_f$ is from 500 to 4000,
A is a substance selected from:
a water-soluble polyhydroxylated substance or compound (X),
a water-insoluble inorganic substance or compound (Y) and wherein it is insoluble in water and oils and oil-repellent.

2. Adduct according to claim 1, wherein it is in semisolid form.

3. Adduct according to said claim 1, wherein the oil is selected from emollient oils, UV sun filters, fragrances, cosmetic and pharmaceutical active ingredients in the form of oils, and mixtures thereof.

4. Adduct according to claim 1, wherein said water-soluble polyhydroxylated substance or compound (X) comprises at least one carboxyl group and the water-insoluble inorganic substance or compound (Y) is in the form of micronized powder.

5. Adduct according to claim 1, wherein said polyhydroxylated substance or compound (X) is selected from lactates, citrates, ascorbates and mixtures thereof.

6. Adduct according to claim 5, wherein said ascorbates are sodium ascorbate or ascorbic acid and mixtures thereof.

7. Adduct according to claim 1, wherein said water-insoluble inorganic substance or compound (Y) is selected from metal oxides, phosphate minerals, silicate minerals and mixtures thereof.

8. A cosmetic treatment of skin comprising:
applying an adduct according to claim 1 to the skin of a subject.

9. A composition comprising at least one physiologically acceptable excipient and an adduct according to claim 1.

* * * * *